United States Patent [19]

Sakurai et al.

[11] Patent Number: 4,863,907
[45] Date of Patent: Sep. 5, 1989

[54] CROSSLINKED GLYCOSAMINOGLYCANS AND THEIR USE

[75] Inventors: Katukiyo Sakurai; Yoshio Ueno; Takashi Okuyama, all of Higashiyamato, Japan

[73] Assignee: Seikagaku Kogyo Co., Ltd., Tokyo, Japan

[21] Appl. No.: 748,729

[22] Filed: Jun. 25, 1985

[30] Foreign Application Priority Data

Jun. 29, 1984 [JP] Japan .................. 59-132885
Jan. 17, 1985 [JP] Japan .................. 60-4908
Jan. 22, 1985 [JP] Japan .................. 60-8512
Jan. 29, 1985 [JP] Japan .................. 60-13595

[51] Int. Cl.$^4$ .............. A61K 31/70; C07B 37/10; C07H 15/00
[52] U.S. Cl. ..................... 514/56; 536/1.1; 536/18.7; 536/21; 536/4.1; 514/54
[58] Field of Search ............ 536/1.1, 21, 18.7; 514/54, 56

[56] References Cited

U.S. PATENT DOCUMENTS

| | | | |
|---|---|---|---|
| 3,507,851 | 4/1970 | Ghetie et al. | 536/54 |
| 3,829,412 | 8/1974 | Kunz. | |
| 4,098,859 | 7/1978 | Cummisford et al. | |
| 4,470,975 | 9/1984 | Berger et al. | |
| 4,532,267 | 7/1985 | Allan. | |
| 4,582,865 | 4/1986 | Balazs et al. | 536/4.1 |

FOREIGN PATENT DOCUMENTS

0185208 11/1982 Japan.
0084225 5/1985 Japan.

OTHER PUBLICATIONS

Acta Chemica Scandinavica, vol. 18, 1964, Part 1.

*Primary Examiner*—Johnnie R. Brown
*Assistant Examiner*—Elli Peselev
*Attorney, Agent, or Firm*—Frishauf, Holtz, Goodman & Woodward

[57] ABSTRACT

Crosslinked glycosaminoglycans or salts thereof prepared by crosslinking glycosaminoglycan or salts thereof with a polyfunctional epoxy compound wherein a crosslinking index is 0.005 or more per 1 mole of repeating disaccharides in glycosaminoglycan, and having various medical and cosmetic uses.

7 Claims, 8 Drawing Sheets

CROSSLINKED GLYCOSAMINOGLYCANS AND THEIR USE

BACKGROUND OF THE INVENTION

This invention relates to a crosslinked glycosaminoglycan. More particularly, it is concerned with a crosslinked glycosaminoglycan or salt thereof, which is prepared by crosslinking a glycosaminoglycan (hereinafter referred to as "GAG") or a salt thereof with a polyfunctional epoxy compound.

As GAG which has been hitherto found in this field, there may be mentioned as non-sulfated GAG hyaluronic acid and chondroitin (hereinafter referred to as "Ch"), while there are known as sulfated GAG chondroitin sulfate (hereinafter referred to as "ChS"), heparin (hereinafter referred to as "Hep"), heparan sulfate (hereinafter referred to as "HS"), keratan sulfate (hereinafter referred to as "KS"), and keratanpolysulfate (hereinafter referred to as "KPS"). Also, ChS may includes ChS-A, ChS-B, ChS-C, Ch-S, ChS-E, ChS-F and ChS-H.

It has been recently elucidated that such GAG's may participate in development, growth, aging or diseased state of various tissues or cells and play an important role, respectively. Generally, it has been reported that GAG has functions of (1) control of water or electrolytes in extracellular fluids, (2) calcification, (3) fibrosis, (4) wound healing and granulation, (5) infection resistance, (6) lubrication, (7) anticoagulation and antilipemia, (8) maintenance of transparency and others.

In order that those functions of GAG itself as depicted above may be developed, there has been attempted external administration of GAG to a living body. However, only a weak effect could be sometimes attained, no effect could be observed or an effect could be developed at an undesired or inconvenient site or portion in some instances. The reasons therefor are believed to be the facts that the GAG externally administered had a lower molecular weight during its purification procedures than that when present in a living body, and the GAG did not form any inherent protein complex in a living body, thereby the GAG being very soluble in water and easily subjected to enzymatic decomposition, and then the GAG would disappear before development of its functions without any retention at local sites or diffuse into other inconvenient sites.

For solving such disadvantageous problems, there have been proposed that GAG be bound to an amino acid, a peptide, a protein or the like or combined with a suitable fat-soluble group. However, any one of them has not yet been practically embodied in view of antigenicity or a quite different property developed.

On the other hand, it has been suggested to crosslink dextran or agarose with a crosslinking agent as disclosed in Japanese Patent Published Application No. Sho 47-1321 (or No. 1321/1972); there has not, however, been reported any instance crosslinking GAG, for the purpose of solving above-mentioned disadvantages.

Under these circumstance, we have made earnest studies to obtain a crosslinked GAG having resistance to enzymatic decomposition and, as a result, it has been found that the intended objects can be achieved by crosslinking GAG or a salt thereof with a polyfunctional epoxy compound Further, it has been found that the present crosslinked GAG or salts thereof can have a wide variety of medical and cosmetic uses.

SUMMARY OF THE INVENTION

It is, accordingly, a primary object of this invention to provide a novel crosslinked GAG or salts thereof which can show many useful properties.

Another object of this invention is to provide new uses of the present crosslinked GAG or salts thereof as medicines, especially, a vitreous body treating agent or a medical device or as skin cosmetics.

According to this invention, there is provided a crosslinked GAG or a salt thereof obtainable by crosslinking a GAG (provided that hyaluronic acid is excluded) or a salt thereof with a polyfunctional epoxy compound wherein a crosslinking index is 0.005 or more per 1 mole of repeating disaccharides in GAG.

As the GAG which may be employed in this invention, there may be mentioned Ch, ChS (including A, B, C, D, E, F and H), Hep, HS, KS and KPS. With regard to hyaluronic acid, we disclosed and claimed in our copending Japanese Patent Application No. 59-88440 for the corresponding crosslinked hyaluronic acid or salts thereof and its applicable uses.

Those GAG's employed for this invention may be commercially available and satisfactorily usable. The GAG employed for this invention, if any corresponding salt will be formed, may be employed in the form of a salt thereof. As the GAG salt, there may be mentioned an alkali metal salt such as sodium or potassium salt and an alkaline earth metal salt such as calcium or magnesium salt.

As used herein, the term "polyfunctional epoxy compound" is meant to indicate the compound which has at least one epoxy group and, further, one or more functional groups suitable for crosslinking GAG including epoxy groups.

As such compounds, there may be exemplified by a halomethyloxirane compound, a bisepoxy compound and the like. As the halomethyloxirane compound, there may be mentioned, for example, epichlorohydrin, epibromohydrin, β-methylepichlorohydrin, β-methylepibromohydrin and the like. As the bisepoxy compound, there may be mentioned, for example, 1,2-bis(2,3-epoxypropoxy)ethane, 1,4-bis(2,3-epoxypropoxy)butane, 1,6-bis(2,3-epoxypropoxy)hexane and a diglycidyl ether of bisphenol A or bisphenol F.

The crosslinked GAG of this invention may be prepared, for instance, according to the process as disclosed in our copending Japanese Patent Application No. Sho 59-88440 (or No. 88440/1984), the disclosure of which is incorporated herein by reference.

Alternatively and preferably, the crosslinked GAG of this invention may be prepared according to the under-mentioned process with a more efficient reaction. More specifically, to an alkali solution of GAG or a salt thereof is added a water-soluble organic solvent and the resulting sticky precipitate is separated. To said precipitate is added a polyfunctional epoxy compound, and reaction can be carried out at a temperature of 50° C. or lower to accomplish a very efficient reaction.

An aqueous alkali solution has preferably a pH of 8-14, more preferably a pH of 12-14. As the alkali, there may be usually mentioned an alkali or alkaline earth metal hydroxide such as sodium hydroxide, potassium hydroxide, lithium hydroxide or calcium hydroxide; an alkali or alkaline earth metal carbonate such as sodium carbonate or potassium carbonate. As the water-soluble organic solvent, there may be mentioned, for example, methanol, ethanol, isopropanol, acetone or dioxane; it may be used alone or in combination therewith. By addition of said water-soluble organic solvent, there can be formed in situ a sticky precipitate, which may be easily recovered, for example, by decantation to remove supernatant. Reaction temperature is usually 10°–50° C., most preferably 20°–40° C. As the higher reaction temperature is, the shorter reaction should be completed. In general, it is preferred that approximately 2 hours may be at about 40° C., while 24–48 hours at about 20° C.

In this reaction, a crosslink index or crosslinking degree in the resultant crosslinked GAG or salt thereof may be suitably controlled by varying a molar ratio of GAG or a salt thereof to a polyfunctional epoxy compound.

In order to obtain the desired crosslinked GAG having a crosslinking index of not less than 0.005 per 1 mole of repeating disaccharides in GAG, it is satisfactory to employ 0.1 mole or more of a polyfunctional epoxy compound to 1 mole of repeating disaccharides in GAG.

In a GAG having a molecular weight of 10,000 to 100,000, when the crosslinking index is in the range of 0.005 to 0.165 relative to 1 mole of repeating disaccharides in the GAG, there can be obtained a crosslinked GAG having water-solubility and stringiness (hereinafter frequently referred to as "s-crosslinked GAG").

On the other hand, when said crosslinking index is 0.165 or more relative to 1 mole of repeating disaccharides in the GAG, there can be prepared a water-insoluble, gel-like crosslinked GAG (hereinafter frequently referred to as "is-crosslinked GAG").

The alternative process for preparing crosslinked GAG by separating a sticky precipitate including GAG has an advantage that a crosslinking agent, a polyfunctional epoxy compound, may be efficiently utilized for reaction and thus an amount of the crosslinking agent applied may be extremely small.

The crosslinked GAG or salt thereof according to this invention can show resistance to glycosidase and also retain a variety of properties which GAG itself has originally so that the present crosslinked GAG or salt thereof may have a wide variety of uses as described hereinbelow in detail. It is also contemplated that such various uses of the crosslinked GAG or salt thereof fall within the perview of this invention.

As one application, the present crosslinked GAG may be employed as ophthalmologic drugs, especially a vitreous body treating agent.

In application as a vitreous body agent, the crosslinked GAG is usually dissolved in physiological saline at such a sufficient viscosity to pass through an injection needle, i.e., not more than 50000 cp, more preferably 5000–30000 cp (20° C., slide speed 1 sec$^{-1}$). Injection may be accomplished, for example, according to Scott method, injection under twin inverted image ophthalmologic scopic examination with silicon oil (J. D. Scott, Trans. Ophthalmol. Soc. U.K., 93, 417, 1973). The present vitreous body agent may be applied to patients without taking the prone position. The present agent may be useful for treatment of difficult retinal detachment to treat and restore, i.e., retinal ablation with proliferation retinopathy of vitreous body, retinal detachment with huge dehiscence, proliferation traction retinal detachment or dehiscence-originated retinal detachment with diabetic retinopathy.

In another application, the present crosslinked GAG may be applied as cosmetics.

In the present skin cosmetics, the crosslinked GAG may be preferably incorporated into cosmetics at 0.01–3% upon a whole cosmetic composition.

The present cosmetics may be optionally blended with other cosmetic additives such as a water-soluble thickening agent, a surface active agent, an oil humectant, an ultraviolet absorbing agent, an alcohol, a chelating agent, a pH adjusting agent, an antiseptic agent, a pigment and a perfume.

As the water-soluble thickening agent, there may be mentioned, for example, a polyamino acid or a salt thereof; a polyacrylic acid or a salt thereof; pulurane; carboxymethylcellulose; xanthan gum and the like. Such water-soluble thickening agent may be usually employed alone or in admixture with the two or more and may be incorporated at 0.01–5% upon a whole cosmetic composition.

Also, the present skin cosmetics may be blended with allantoin or its derivative which may be employed as a dermatological disease treating agent or a raw material for cosmetic industry. In this instance, it may be preferably incorporated at 0.01–5%.

The present cosmetics can show an excellent water retention and an excellent resistance to enzymes.

The present cosmetics may be applied, for example, after shaving, chaps, cracks, chappy skin and so on in the form of cosmetics such as creams, e.g. a nutrient cream, a hand cream, a body cream, a massage cream; nutrient milky lotions; face packs; face lotions, as well as hair cosmetics.

As a still another application, the present crosslinked GAG may be utilized as various medical devices. In this instance GAG may be also applied in the form of a complex with collagen (hereinafter referred to as "CO").

In molding a medical device with the present molding materials, the present molding material is placed into a desired die, dehydrated and then dried.

A molded product may be of any shape, preferably in the shape of a film. There is no limitation to molding procedures, and casting is preferable.

An aqueous solution or suspension of the present molding material may be coated over a polymer, e.g., polyethylene sheet or film or a support, e.g., glass or metal plate to a desired thickness by means of an applicator, dehydrated and dried and then peeled off from said sheet, film or support to produce a film molded product.

A medical device obtained from the present molding material when dipped in water or physiological saline may gradually absorb water and may be dissolved. In a living body, the dissolved product may be decomposed with enzymes and the like and, therefore, if a crosslinking index may be controlled, it could be present within a living body or skin only over a necessary period and dissolved away from tissues as lacked tissues will be healed.

The present crosslinked GAG, when given or applied to a living body, does not show any foreign body reaction and, when applied as a medical device, can show a very high safety.

In addition to the foregoing, the present crosslinked GAG, especially s-crosslinked GAG may also show an excellent sustained release effect and thus is useful for the preparation of sustained release drugs. Also, is-crosslinked GAG may have a good affinity to collagen or antithrombin III (hereinafter referred to as "AT III")

and is, therefore, useful, for example, as a carrier of affinity chromatography therefor and so on.

DESCRIPTION OF PREFERRED EMBODIMENT

This invention will be more fully illustrated by way of the following examples, but they are not construed to be limiting the scope of this invention.

EXAMPLE 1

(1) Synthesis of s-crosslinked GAG (ChS-C)

To a 12.5% solution of 3.1 g of ChS-C sodium salt (molecular weight: 53000) in a 0.75 N aqueous solution of sodium hydroxide was added 1 volume of ethanol under stirring and the resultant sticky precipitate was separated and recovered. To this sticky precipitate was added 0.18 ml of epichlorohydrin, the resulting mixture was kneaded well and then it was allowed to stand at 20° C. for 24 hours. To the reaction mixture were added 30 ml of water, the resulting solution was adjusted to pH 6.0 with acetic acid and precipitation was carried out with ethanol. Dissolution in water and precipitation with ethanol were repeated again and distillation was done under reduced pressure.

| | |
|---|---|
| Yield | 2.9 g |
| Crosslinking index per 1 mole of repeating disaccharides in ChS—C | 0.101 |
| Viscosity in 10% physiological saline (20° C., slide speed 1.0 sec$^{-1}$) | 45200 centipoises (cp) |
| Elemental analysis: (%) C: 33.31, H: 3.78, N: 2.72, S: 6.35, Na: 9.25 | |

(2) Gel chromatography of s-crosslinked GAG (ChS-C)

Using the s-crosslinked GAG (ChS-C sodium salt) as synthesized in the above (1) and the ChS-C employed for said synthesis, gel chromatography was performed with a column (6×850 mm) of glass beads CPG 3000 (Electro Nucleonics Inc.). A 1.5M aqueous solution of sodium chloride was adjusted to pH 8.5 with sodium hydroxide and employed as a developing solvent. Each 0.52 ml of eluted fractions was separated and determined for uronic acid according to a carbazole-sulfuric acid method. The results are shown in FIG. 1, wherein the hollow circle () and full circle (•) show absorbance in each fraction of the s-crosslinked GAG (ChS-C) and ChS-C, respectively, according to a carbazole-sulfuric acid method.

Figure 1:
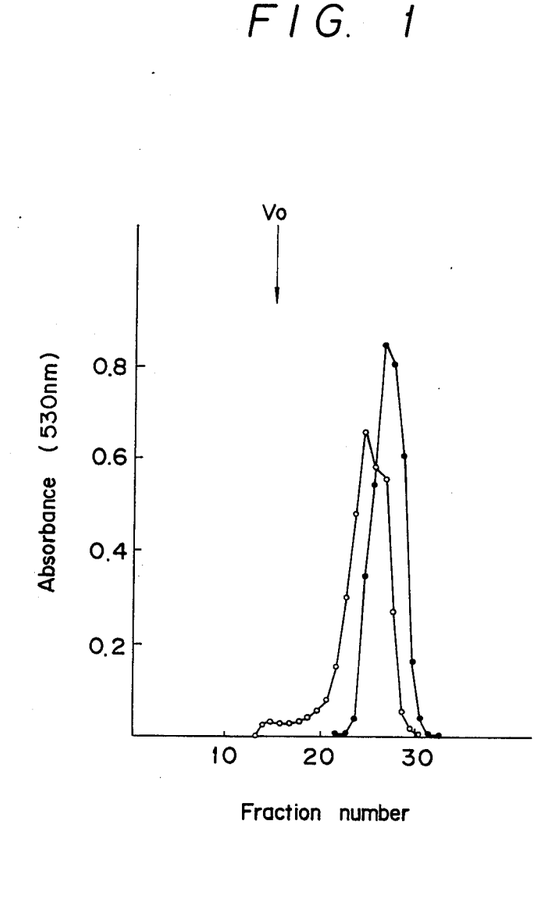

It is apparent from FIG. 1 that the present s-crosslinked GAG is of a very high molecular weight, as compared with the starting GAG.

(3) Sustained release effect of s-crosslinked GAG (ChS-C)

The s-crosslinked GAG (ChS-C) as synthesized in the above (1) and starting ChS-C in 1% physiological saline were tested for substained release effect to drugs by using a dialysis film, Visking tube (available from Visking Company, 18/32) and a 1% physiological saline solution of p-nitrophenol (hereinafter frequently referred to as "PNP solution").

In dialysis films were placed (5 ml of physiological saline+1 ml of PNP solution), (5 ml of 1% s-crosslinked GAG or ChS-C solution+1 ml of PNP solution) and (5 ml of 1% ChS-C solution+1 ml of PNP solution), respectively, and said films were evacuated and sealed. Recovery of PNP dialyzed into external dialysis liquid (200 ml of physiological saline) was determined by measuring absorbance at 315 nm. The results are shown in FIG. 2, wherein the full circle (•), hollow circle () and dotted circle (⊙) represent, respectively, influence upon PNP dialysis of physiological saline, ChS-C and s-crosslinked ChS-C.

Figure 2:
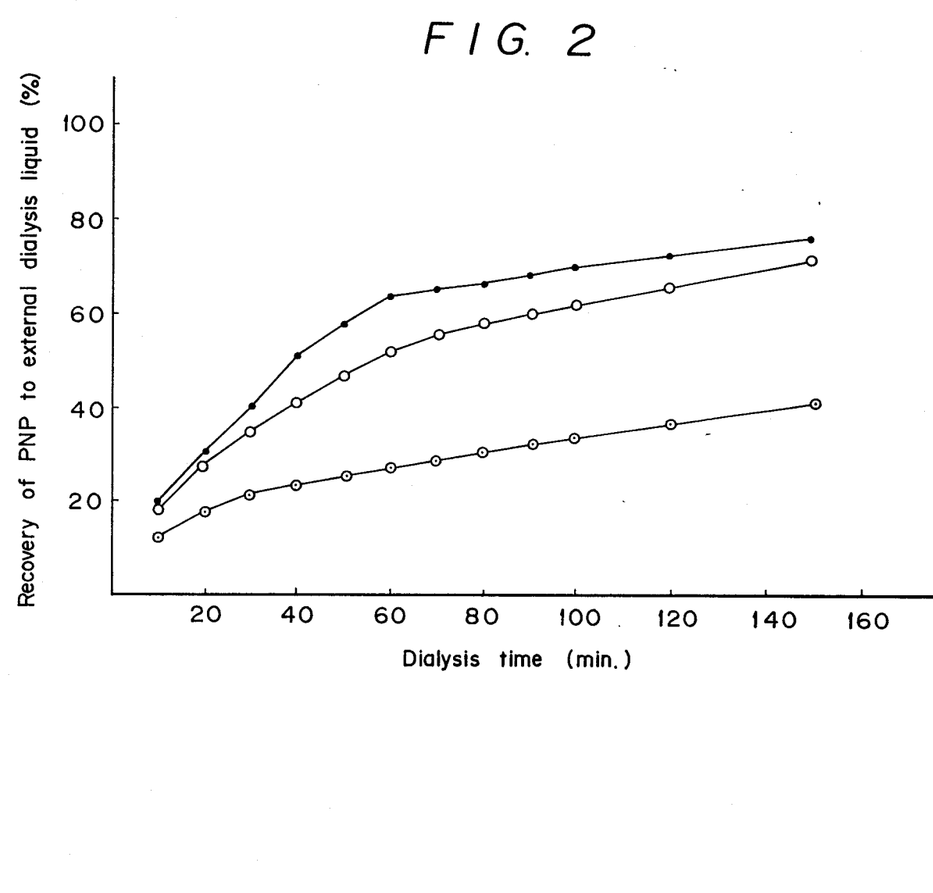

It is apparent from the results as shown in FIG. 2 that the present s-crosslinked GAG is effective for sustanined release of drugs.

(4) Resistance to glycosidase of s-crosslinked GAG (ChS-C)

Two sorts of s-crosslinked ChS-C's were synthesized ChS-C sodium salt (molecular weight: 53000) according to the procedures of Example 1, (1).

s-crosslinked ChS-C (A)

| | |
|---|---|
| Crosslinking index per 1 mole of repeating disaccharides in ChS—C | 0.07 |
| Viscosity in 10% physiological saline (20° C., slide speed 1.0 sec$^{-1}$) | 3200 cp |
| Elemental analysis: (%) C: 33.4, H: 3.81, N: 2.79, S: 6.34, Na: 9.01 | | s-crosslinked ChS-C (B)

| | |
|---|---|
| Crosslinking index per 1 mole of repeating disaccharides in ChS—C | 0.09 |
| Viscosity in 10% physiological saline (20° C., slide speed 1.0 sec$^{-1}$) | 15000 cp |
| Elemental analysis: (%) C: 33.38, H: 3.75, N: 2.82, S: 6.40, Na: 9.26 | |

The s-crosslinked ChS-C's of Example 1(1) and of the said two sorts and the ChS-C sodium salt employed for synthesis, respectively, were dissolved in 0.4M Tris hydrochloric acid buffer (pH 8.0) to a concentration of 10% and viscosity was measured (20° C., slide speed 1.0 sec$^{-1}$) to obtain the following results, wherein the s-crosslinked ChS-C of Example 1, (1) is represented in terms of s-crosslinked ChS-C (C).

| | |
|---|---|
| s-crosslinked ChS—C (A) | 3100 cp |
| s-crosslinked ChS—C (B) | 14500 cp |
| s-crosslinked ChS—C (C) | 44000 cp |
| ChS—C sodium salt | 1500 cp |

To the solution was added chondoroitinase ABC at 0.05% by weight, reaction was performed at 37° C. and viscosity was measured after 5, 10, 20, 30, 60 and 120 minutes. Proportions to the viscosity before reaction were calculated. The results are shown in FIG. 3, wherein the hollow circle (), open triangle (Δ), open square (□) and full circle (•) represent proportions to the viscosity before reaction at each reaction time with regard to 0.4 M Tris hydrochloric acid (pH 8.0) solutions of the s-crosslinked ChS-C (A), (B) and (C) and of the ChS-C sodium salt, respectively.

Figure 3:
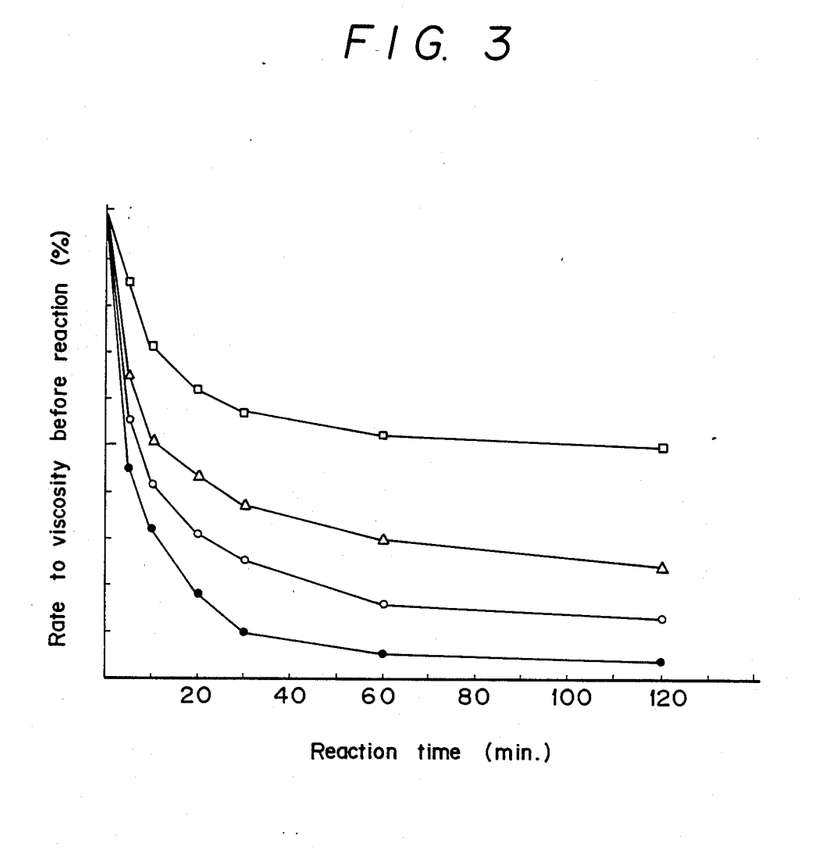

It is apparent from FIG. 3 that the present s-crosslinked ChS-C shows a higher resistance to chondoroitinase ABC as compared with the ChS-C and the higher its crosslinking index is, the more remarkable its resistance is. Similarly, it would be readily inferable that other s-crosslinked GAG's have a resistance to glycosidase.

(5) Stringiness of s-crosslinked ChS

Stringiness of the s-crosslinked ChS-C(A) and ChS-C(B), and a 2% physiological saline solution of sodium salt of ChS-C used for the synthesis was measured by means of an apparatus modeled after Watanabe stringiness measurement apparatus (Hiroshi Ikeuchi, Journal of Orthopedic Surgery of Japan 34, 175, 1960).

When measured at a draw-up speed of 7 cm/sec, the following results were obtained.

|  | Stringiness (cm) |
| --- | --- |
| s-crosslinked ChS—C (A) | 2.8 |
| s-crosslinked ChS—C (B) | 3.1 |
| sodium salt of ChS—C | 0 |

From the above results, it can be understood that the s-crosslinked ChS according to this invention exhibits high stringiness.

EXAMPLE 2

Synthesis of s-crosslinked GAG (ChS-C)

To a 12.5% solution of 1.25 g of ChS-C sodium salt (molecular weight: 54000) in a 0.75 N aqueous solution of sodium hydroxide was added 1 volume of ethanol under stirring and the resulting sticky precipitate was separated and recovered. To this sticky precipitate was added 0.59 ml of epichlorohydrin and the resultant mixture was kneaded well and then allowed to stand at 20° C. for 24 hours. The reaction mixture was dissolved in 15 ml of water, the resulting solution was adjusted to pH 6.0 with acetic acid and precipitation was carried out with ethanol. Dissolution in water and precipitation with ethanol were repeated again and drying was done under reduced pressure.

| Yield | 1.2 g |
| --- | --- |
| Crosslinking index per 1 mole of repeating disaccharides in ChS—C | 0.160 |
| Viscosity in 10% physiological saline (20° C., slide speed 1.0 sec$^{-1}$) | 77500 cp |
| Elemental analysis: (%) C: 33.48, H: 3.90, N: 2.70, S: 6.43, Na: 9.21 | |

EXAMPLE 3

Synthesis of s-crosslinked GAG (Hep)

To a solution of 0.4 g of Hep sodium salt (molecular weight: 15000) in 1 ml of a 1.3 N aqueous solution of sodium hydroxide were added 1.5 ml of ethanol and the resulting sticky precipitate was separated and recovered. To this sticky precipitate was added 0.026 ml of epichlorohydrin, the resulting mixture was kneaded well and reaction was performed at 20° C. for 24 hours. To the reaction mixture were added 5 ml of water, the resulting solution was neutralized with acetic acid and ethanol was added. The white powder thus formed was dried under reduced pressure.

| Yield | 0.37 g |
| --- | --- |
| Crosslinking index per 1 mole of repeating disaccharides in Hep | 0.125 |
| Limiting viscosity (dissolved in 0.2 M NaCl and determined by Ostward's viscometer) | 0.58 (Startig Hep: 0.17) |
| Elemental analysis: (%) C: 23.50, H: 2.61, N: 2.38, S: 13.20, Na: 13.25 | |

EXAMPLE 4

Synthesis of s-crosslinked GAG (ChS-A)

In a 0.75 N aqueous sodium hydroxide solution was dissolved 6.2 g of ChS-A sodium salt having a molecuar weight: 30,000 so that the concentration thereof might be 12.5%. With stirring, 1.2 fold volume of ethanol was added to the solution and then the resulting highly viscous precipitates were separated. To the thus obtained highly viscous precipitates was added 0.6 g of epibromohydrin, and the resulting mixture was kneaded sufficiently and allowed to stand at 20° C. for 24 hours. To the resulting reaction mixture was added 60 ml of water to cause dissolution and the resulting solution was adjusted to pH 6.0, followed by precipitation with ethanol. The precipitates were dissolved again in water, followed by precipitation with ethanol and drying under reduced pressure.

| Yield | 5.8 g |
| --- | --- |
| Viscosity of a 10% physiological saline solution (20° C., slide speed 1.0 sec$^{-1}$) | 28,000 centipoise |
| Elementary analysis: (%) C: 33.54, H: 3.82, N: 2.78, S: 6.13, Na: 9.30 | |

EXAMPLE 5

(1) Synthesis of is-crosslinked GAG (ChS-C)

To a solution of 6.25 g of ChS-C sodium salt (molecular weight: 53000) in 50 ml of a 0.75 N aqueous solution of sodium hydroxide was added 1 volume of ethanol to afford a sticky precipitate. To this sticky precipitate was added 0.49 ml of epichlorohydrin and the resulting mixture was kneaded well and allowed to stand at 20° C. for 36 hours. To the reaction mixture were added 50 ml of water and the resulting mixture was neutralized with acetic acid and then centrifuged at 3000 rpm. The white precipitate thus formed was washed twice with each 50 ml portion of a 2.0M aqueous solution of sodium chloride and then three time with each 50 ml portion of water, dehydrated with ethanol and then dried under reduced pressure.

| Yield | 6.2 g |
| --- | --- |
| Crosslinking index per 1 mole of repeating disaccharides in ChS—C | 0.170 |
| Elemental analysis: (%) C: 33.51, H: 4.01, N: 2.85, S: 6.22, Na: 9.00 | |

(2) Synthesis of is-crosslinked GAG (ChS-A)

In a 0.4 N aqueous solution of sodium hydroxide were dissolved 5.0 g of ChS-A sodium salt (molecular weight: 30000) at a concentration of 20%. By addition of 25 ml of ethanol, the sticky precipitate thus formed was separated and recovered. To the precipitate was added 0.75 ml of epichlorohydrin and the resulting mixture was kneaded well and allowed to stand at 20° C. for 24 hours.

To the reaction mixture were added 50 ml of water, the resulting mixture was neutralized with acetic acid and centrifuged at 3000 rpm. The so-formed white precipitate was washed twice with each 50 ml portion of a 2.0M aqueous solution of sodium chloride and then three times with each 50 ml portion of water, dehydrated with ethanol and then dried under reduced pressure.

| | |
|---|---|
| Yield | 5.0 g |
| Crosslinking index per 1 mole of repeating disaccharides in ChS—A | 0.25 |
| Elemental analysis: (%) | |
| C: 3.31, H: 3.77, N: 2.72, S: 6.45, Na: 9.22 | |

(3) Synthesis of is-crosslinked GAG (Hep)

To a solution of 4.0 g of Hep sodium salt (molecular weight: 15000) in 10 ml of a 1.3 N aqueous solution of sodium hydroxide were added 15 ml of ethanol to give a sticky precipitate. To this sticky precipitate was added 0.4 ml of epichlorohydrin and the resulting mixture was kneaded well and reaction was performed at 20° C. for 24 hours. To the reaction mixture were added 50 ml of water, the resulting mixture was neutralized with acetic acid and then centrifuged at 3000 rpm. The precipitate thus formed was washed twice with each 50 ml portion of a 2M aqueous solution of sodium chloride and then three times with each 50 ml portion of water, dehydrated with ethanol and then dried under reduced prssure to give a white powder.

| | |
|---|---|
| Yield | 3.87 g |
| Crosslinking index per 1 mole of repeating disaccharides in Hep | 0.20 |
| Elemental analysis: (%) | |
| C: 22.55, H: 2.63, N: 2.32, S: 13.16, Na: 13.21 | |

(4) Synthesis of is-crosslinked GAG (ChS-B)

To a solution of 0.225 g of ChS-B (also called dermatan sulfate) sodium salt (molecular weight: 19000) in 5 ml of a 0.36 N aqueous solution of sodium hydroxide were added 10 ml of ethahol to give a sticky precipitate. To the sticky precipitate was added 0.18 ml of epichlorohydrin, the resulting mixture was kneaded well and reaction was performed at 20° C. for 24 hours. To the reaction mixture were added 10 ml of water, the resulting mixture was neutralized with acetic acid and centrifuged at 3000 rpm. The precipitate thus formed was washed twice with each 10 ml portion of a 2M aqueous solution of sodium chloride and then three times with each 10 ml portion of water, dehydrated with ethanol and then dried under reduced pressure to give a white powder.

| | |
|---|---|
| Yield | 0.2 g |
| Crosslinking index per 1 mole of repeating disaccharides in ChS—B | 0.28 |
| Elemental analysis: (%) | |
| C: 32.9, H: 3.80, N: 2.72, S: 6.49, Na: 9.20 | |

(5) Synthesis of is-crosslinked GAG (ChS-B)

To a solution of 0.225 g of ChS-B (also called dermatan sulfate) sodium salt (molecular weight: 19000) in 5 ml of a 0.36 N aqueous solution of sodium hydroxide were added 10 ml of ethanol to give a sticky precipitate. To this sticky precipitate was added 0.2 ml of epibromohydrin, the resulting mixture was kneaded well and reaction was performed at 20° C. for 24 hours. To the reaction mixture were added 10 ml of water, the resulting mixture was neutralized with acetic acid and centrifuged at 3000 rpm. The precipitate thus formed was washed twice with each 10 ml portion of a 2M aqueous solution of sodium chloride and then three times with each 10 ml portion of water, dehydrated with ethanol and then dried under reduced pressure to give a white powder.

| | |
|---|---|
| Yield | 0.21 g |
| Crosslinking index per 1 mole of repeating disaccharides in ChS—B | 0.28 |
| Elemental analysis: (%) | |
| C: 32.8, H: 3.75, N: 2.70, S: 6.61, Na: 9.35 | |

(6) Synthesis of is-crosslinked GAG (KPS)

To a solution of 0.27 g of KPS sodium salt (molecular weight: 9500) in 5 ml of a 0.4 N aqueous solution of sodium hydroxide were added 10 ml of ethanol to afford a sticky precipitate. To this sticky precipitate was added 0.04 ml of epichlorohydrin, the resulting mixture was kneaded well and reaction was performed at 20° C. for 24 hours. To the reaction mixture were added 20 l of water, the resulting mixture was neutralized with acetic acid and centrifuged at 3000 rpm. The precipitate thus formed was washed twice with each 20 ml portion of a 2M aqueous solution of sodium chloride and then three times with each 50 ml portion of water, dehydrated with ethanol and then dried under reduced pressure to give a white powder.

| | |
|---|---|
| Yield | 0.25 g |
| Crosslinking index per 1 mole of repeating disaccharides in KPS | 0.21 |
| Elemental analysis: (%) | |
| C: 29.70, H: 3.68, N: 2.58, S: 11.41, Na: 8.20 | |

(7) Affinity of is-crosslinked GAG to atherocollagen

The is-crosslinked GAG's as synthesized in the above (1), (2), (3) and (4) were evaluated for affinity to atherocollagen. 1.1 g of atherocollagen (purchased from Koken K.K.) were dissolved in 1.67 mM acetic acid and passed through GC 90 filter for use (5 mg/ml). In a 15 ml volume test tube were placed approximately 5 mg of the is-crosslinked GAG, which were then suspended in 10 ml of 1.67 mM acetic acid. To the suspension was added 0.5 ml of the atherocollagen solution and the resulting mixture was admixed, thoroughly for 30 minutes. After centrifugation at 3000 rpm, the precipitate thus separated was washed three times with each 10 ml portion of 1.67 mM acetic acid. Washings of 1.67 mM acetic acid were collected and determined for collagen. Bound collagen was eluted by admixing with 10 ml of 2M guanidine-hydrochloric acid (pH 7.0) over 40 minutes and subsequently centrifuging at 3000 rpm. Further elution was done twice with each 10 ml portion of the said buffer. All guanidine-hydrochloric acid eluates were collected and determined for collagen. The results are shown in Table 1.

It is apparent from the results that GAG when crosslinked could retain inherent properties of GAG itself.

TABLE 1

| is-cross-linked GAG | Amount employed (mg) | Un-adsorbed collagen (mg) | Adsorbed collagen All adsorbed amount (mg) | Adsorbed amount per 1 mg of is-crosslinked GAG (mg) | All collagen recovery (%) |
|---|---|---|---|---|---|
| ChS—C | 6.6 | 0.14 | 2.20 | 0.33 | 93.6 |
| ChS—A | 5.6 | 2.23 | 0.32 | 0.06 | 102.0 |
| Hep | 5.0 | 0.04 | 2.39 | 0.48 | 97.2 |
| ChS—B | 4.9 | 0.62 | 1.90 | 0.39 | 100.8 |

(Collagen amount added: 2.5 mg)

(8) Affinity of is-crosslinked GAG to AT III

The is-crosslinked GAG's as synthesized in the above (1) and (3) were evaluated for affinity to AT III. The AT III derived from rabbit plasma was used and dissolved in a 50 mM Tris hydrochloric acid buffer (pH 7.4) containing 0.05M sodium chloride (hereinafter referred to as "A buffer") at a concentration of 1.67 mg/ml. The AT III solution showed an optical density (O.D.) of 1.0 at 280 nm.

As other buffers, there were employed a 50 mM Tris hydrochloric acid buffer (pH 7.4) containing 0.5M sodium chloride (hereinafter reffered to as "B buffer") and a 50 mM Tris hydrochloric acid buffer (pH 7.4) containing 1.5 M sodium chloride (hereinafter referred to as "C buffer").

Figure 4:
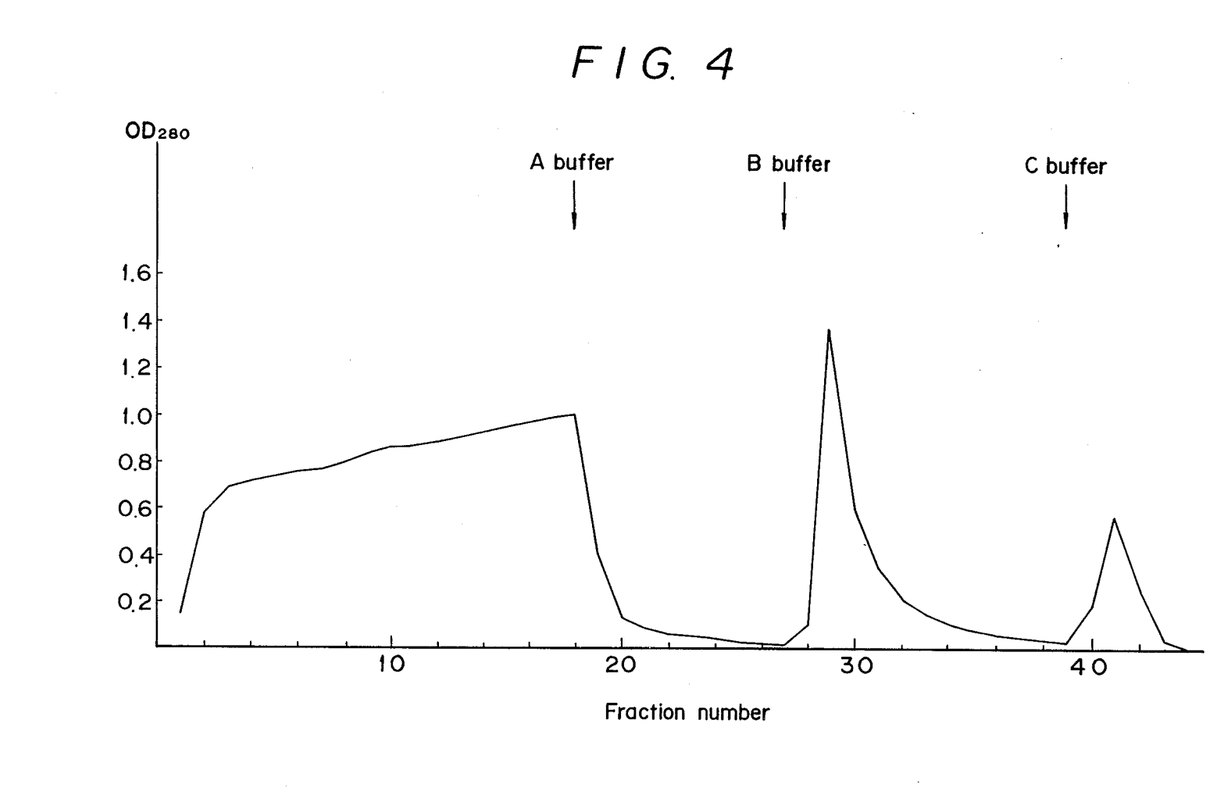

The is-crosslinked GAG was suspended in A buffer, 0.9 ml of the suspension was packed into a column and the AT III solution passed therethrough. When $O.D._{280}$ of eluate reached 1.0, the AT III solution was discontinued to be passed and the column was eluted and washed with A buffer thoroughly. Stepwise elutions were made in turn with B buffer and C buffer and $O.D._{280}$ of eluate was measured. The results of is-crosslinked GAG (Hep) are shown in FIG. 4, wherein each eluted fraction was 2.3 ml. This shows that the AT III was adsorbed at 0.89 g per 1 mg of the is-crosslinked GAG, while the AT III was not adsorbed onto the is-crosslinked GAG(ChS-C).

As apparent from the above, GAG even when crosslinked could retain inherent properties of GAG itself.

EXAMPLE 6

Crosslinking index of crosslinked GAG

In a 0.75 N aqueous sodium hydroxide solution were dissolved 1.25 g of ChS-C sodium salt (molecular weight: 53000) and an equal volume of ethanol was added thereto. Supernatant was discarded and the resultant sticky precipitate was mixed with (2-$^{14}$C)epichlorohydrin (available from Amasham Japan Co., Ltd.) as a $^{14}$C-label compound, the resulting mixtue was kneaded well and allowed to stand at 20 ° C. for 48 hours. Then, 20 ml of water were added to the reaction mixture, pH was adjusted to 6.0 with acetic acid and precipitation was done with a three times volume of ethanol. Next, the precipitate was dissolved in 20 ml of water and the resulting solution was admixed with a three times volume of ethanol to yield a white powder, which was then washed with ethanol and dried under reduced pressure. Water-insoluble is-crosslinked GAG was obtained by adding 20 ml of water to the reaction mixture, centrifuging, thoroughly washing with a 0.5M aqueous solution of sodium chloride and water, dehydrating with ethanol and drying.

To 5 mg of the sample as prepared above was added 0.5 ml of a 1.0 N aqueous solution of sodium hydroxide, the resulting mixture was heated at 30° C. for one hour to reduce viscosity and neutralized with 0.5 ml of 1.0 N hydrochloric acid. The solution was measured for radioactivity by means of a liquid scintillation counter and crosslinking index was calculated. The results are shown in Table 2.

It is apparent from Table 2 that crosslinking index is proportional to viscosity in s-crosslinked GAG.

In this Example, the following materials were employed with resultant yields.

| Sample | Epichlorohydron μ(mM) | Molar ratio Starting material: NaOH: epichlorohydrin | Yield g |
|---|---|---|---|
| A | 58 (0.75) | 1:3:0.3 | 1.25 |
| B | 78 (1.0) | 1:3:0.4 | 1.25 |
| C | 74 (0.95) | 1:3:0.38 | 1.24 |
| D | 93 (1.18) | 1:3:0.47 | 1.24 |
| E | 98 (1.25) | 1:3:0.5 | 1.20 |

{Starting material 1.25 g (2.5 mM), NaOH 0.75 M (total 7.5 mM), EtOH 10 ml, reaction at 20° C. for 48 hours}

TABLE 2

| Radioactivity per 2.5 mg of sample (DPM) | Converted epichlorohydrin per 2.5 mg of sample (μmol) | Crosslinking index per 1 mole of repeating disaccharides in sample | Viscosity in 10% physiological saline (cp) (20° C., slide speed 1.0 sec$^{-1}$) |
|---|---|---|---|
| A 2412 | 0.25 | 0.050 | 1680 |
| B 3215 | 0.34 | 0.068 | 2600 |
| C 4022 | 0.42 | 0.084 | 3500 |
| D 7536 | 0.79 | 0.158 | 76000 |
| E 8039 | 0.84 | 0.168 | water-insoluble |

*Specific activity of (2-$^{14}$C)epichlorohydrin: 4.3 μCi/mmol
*2.5 mg of sample corresponding to 5 μmol of converted repeating disaccharides in ChS

EXAMPLE 7

Replacement of vitreous body by crosslinked ChS and measurement of restoration rate Using a 10% physiological saline solution of crosslinked ChS of Example 1 (1), one conducted the following test.

In 10 rabbits (an average body weight: 3 kg) wherein experimental retinal detachment was brought about by drawing cortical vitreous body with a pincette (an ophthamologic forceps), there was made an exit hole in sclera of right eye to remove fluid under retina, while there was made one incision of pars plana of ciliary body. Under examination by twin—inverted image—ophthalmologic scope, crosslinked ChS of Example 1, (1) was slowly injected by injecting a crosslinked Chs injection needle behind lens. When retina was restored with removal of fluid under retina, injection needle and exit needle were drawn off. Removal and injection were repeated mutually through opposite holes so that a cavity in vitreous body was replaced with the crosslinked ChS as far as possible. After 10 days, restored state was observed by means of funduscopic camera. As a result, retinal detachment was observed to be completely recovered in 7 rabbits (restoration rate, 70%).

EXAMPLE 8

Wound healing effect of crosslinked GAG

Male Wistar-strain rats with 4 weeks of age were used for the following experiment, each group consisting of 6 animals.

Animals were hair-cut with an electric hair-clipper and then intramuscularly injected with pentobarbital sodium. Skin on the back was incised to about 2 cm at right and left parts and incised portions were immediately sewn by means of Michel sewing apparatus. After sewing, a 0.2% physiological saline solution of the crosslinked ChS of Example 1, (1) or a 0.2% physiological saline solution of allantoin was coated over the left part with 0.1 ml once a day over 2 weeks. As control, physiological saline was coated over the right part. After 2 weeks, rats were sacrificed, sewing needles were removed and skin strip was prepared with a width of 2 cm, which each 1 cm was cut right and left at the center of said incision part, and with a length of 1 cm. Tensile strength of skin strip was measured by means of Universal tensile testing instruments TENSILON RTM-50 (available from Toyo-Baldwin K.K.). Wound healing effect was determined from ratios to control. The results are shown in Table 3.

TABLE 3

| Sample | Wound healing effect |
| --- | --- |
| Crosslinked ChS solution | 1.52 |
| Allantoin solution | 1.30 |

EXAMPLE 9

Water retention of crosslinked GAG

In distilled water were dissolved the crosslinked ChS of Example 1, (1), and ChS-C sodium salt (molecular weight: 53000) at a concentration of 5%, respectively. Each 3.0 g of the solutions was placed in a weighing bottle and allowed to stand at 20° C. and relative humidity as prescribed until a constant weight was reached. Residual water content in residue was determined to obtain a water loss of each sample. The results are shown in FIG. 5, wherein the hollow circle (○), full circle (●) and dotted circle (◉), respectively, represent water loss of the crosslinked ChS-1, ChS-C sodium salt and purified water.

Figure 5:
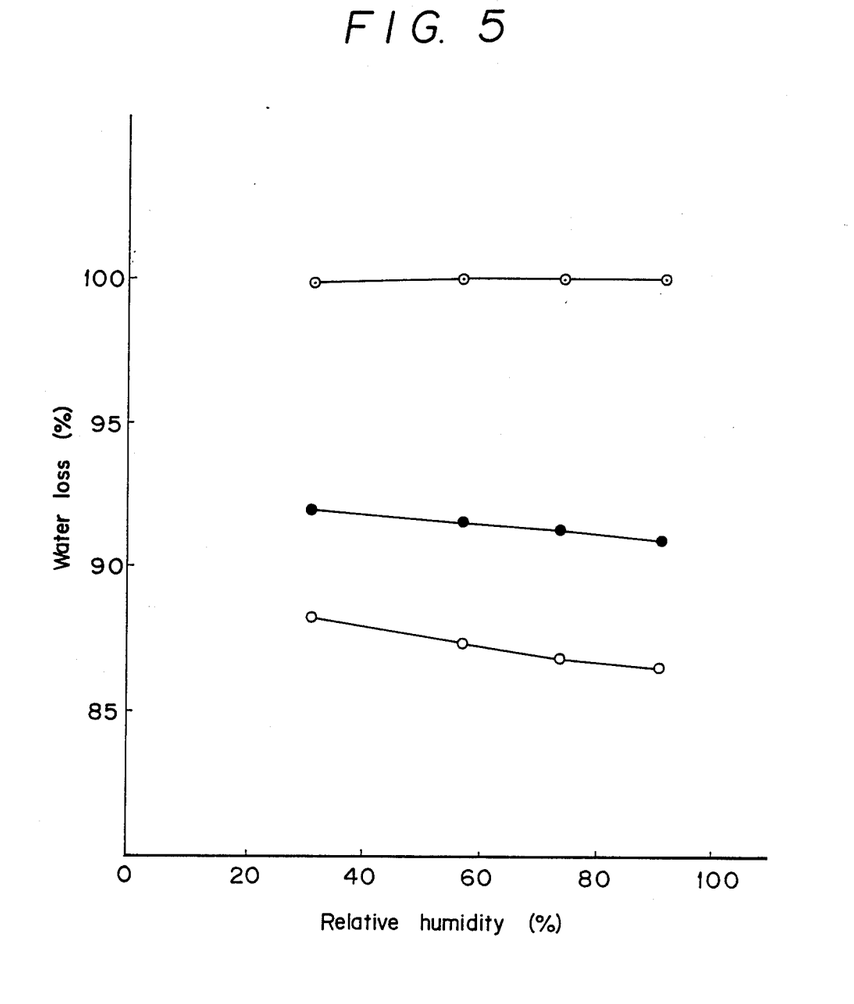

It is apparent from FIG. 5 that the present crosslinked GAG has an excellent water retention.

EXAMPLE 10

Synthesis of s-complex of ChS-C with CO

Substantially following the precedures of Example 1, (1), there were prepared the under-mentioned three types of crosslinked ChS-C's.

| Product | Epichloro-hydrin (ml) | Crosslinking index per 1 mole of repeating disacchari-des in ChS—C | Viscosity of 5% aqueous soln. (cp) (20° C., slide speed 1.0 sec$^{-1}$) |
| --- | --- | --- | --- |
| crosslinked ChS-I | 6.0 | 0.101 | 5550 |
| crosslinked ChS-II | 8.29 | 0.158 | 21000 |
| crosslinked ChS-III | 9.67 | 0.168 | 45000 |

(1) Each 500 mg of the crosslinked ChS-I as above was dissolved in 75 ml of water. To the respective solutons was added under stirring 50 ml of an aqueous solution of atherocollagen at various concentrations (containing 2.5 mg, 6.33 mg, 10.2 mg, 24.9 mg, 49.45 mg and 100.6 mg of CO, respectively) and the mixture was allowed to stand at 20° C. for 30 minutes. After centrifugation at 3000 rpm for 30 minutes, supernatant was freeze-dried. The freeze-dried product was measured for uronic acid recovery according to a carbazole-sulfuric acid method. Also, a similar test was conducted with a 0.67% aqueous solution of ChS-C (molecular weight: 30000). The results are shown in FIG. 6, wherein the hollow circle (○) and full circle (●), respectively, represent uronic acid recovery in supernatant when the s-crosslinked ChS-C and ChS-C were employed.

Figure 6:
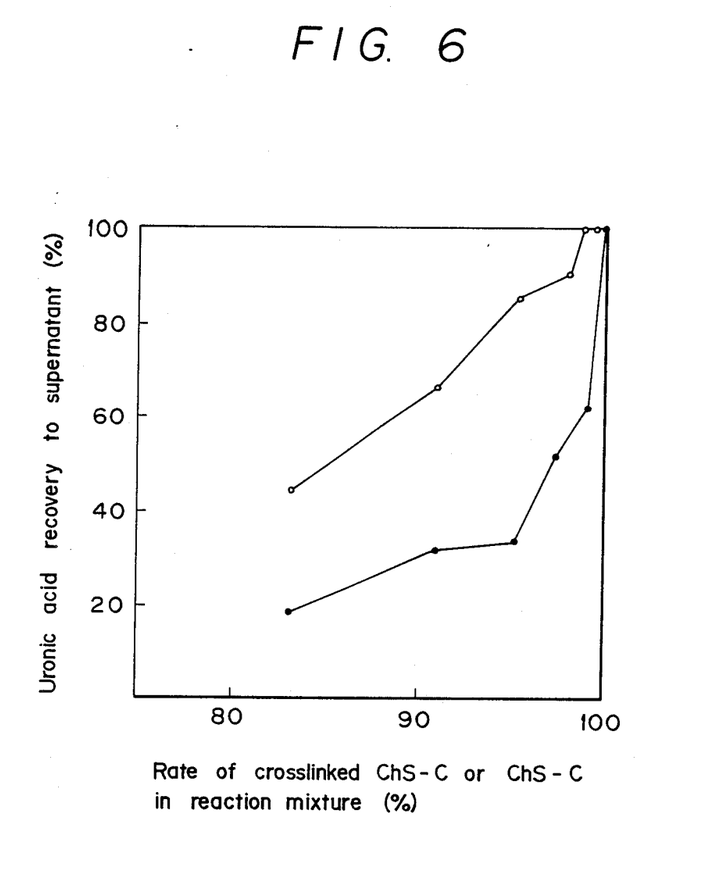

It is apparent from FIG. 6 that ChS-C is reacted with CO to form a complex which becomes instantly water-insoluble, whereas the s-crosslinked ChS-C can retain water-solubility even when combined with a considerable amount of CO.

The s-complex as obtained above was measured for viscosity and the results are shown in Table 4.

TABLE 4

| | Crosslinked ChS—C or ChS—C content in freeze-dried product (%) | Viscosity in 5%, 0.15 M aqueous soln. of NaCl (cp) (20° C., slide speed 1.0 sec$^{-1}$) |
| --- | --- | --- |
| Cross-linked ChS—C | 99.5 | 6500 |
| | 98.5 | 29000 |
| | 93.5 | 245000 |
| | 92.5 | 100000 |
| | 87.0 | 25500 |
| | 68.5 | 130000 |
| ChS—C | 99.5 | 910 |
| | 98.0 | 900 |
| | 95.0 | 3950 |
| | 86.0 | 13000 |
| | 62.0 | 50000 |

(2) An s-complex of crosslinked ChS-I with CO was prepared under the condition to provide a complex with the maximum viscosity, i.e., to provide a crosslinked ChS-I content of 94% in a freeze-dried product.

| Yield | 98.4% |
| --- | --- |
| ChS—C content | 94.7% |
| Viscosity in 5% physiological saline (20° C., slide speed 1.0 sec$^{-1}$) | 244000 cp |

EXAMPLE 11

(1) Preparation of crosslinked ChS-C film

Using a 7.5% aqueous solution of the crosslinked ChS-I, -II or -III as prepared in Example 10, there were prepared the crosslinked ChS-C films as follows:

The aqueous solution was coated over a polyvinyl chloride plate to a certain thickness by means of an applicator and dehydrated by heating with a hot air at 40° C. for 20 hours. Each coated film was peeled off to form a film with a thickness of 0.003 cm. Also, a 10% aqueous solution of ChS-C (molecular weight: 53000) was treated in the same manner as above to form a ChS-C film with a thickness of 0.003 cm as control.

Tensile resistance of the film was measured by means of Universal tensile testing instruments TENSILON RTM-50 (available from Toyo-Baldwin K.K.). The results are shown in Table 5.

TABLE 5

| Crosslinked ChS film | Water content (%) | Tensile resistance (kg/cm) |
|---|---|---|
| ChS-I | 15.4 | 0.57 |
| ChS-II | 15.3 | 2.00 |
| ChS-III | 15.0 | 0.74 |
| Control | 10.4 | 0.48 |

(2) Solubility test of film

To 5 mg of each film as prepared in the above (1) were added in a test tube 10 ml of physiological saline and the resulting mixture was allowed to stand for 30 minutes. Test tube was vigorously shaken up and down 20 times and then allowed to stand for one day. Again, test tube was vigorously shaken up and down 20 times and then centrifuged at 3000 rpm for 30 minutes. 0.1 ml of supernatant was recovered and determined for uronic acid according to the carbazole-sulfuric acid method to determine elution rate.

Once again, test tube was vigorously shaken up and down 20 times and then allowed to stand for one day. Thereafter, elution rate was determined in the same manner as above. The aforesaid procedures were repeated for 18 days.

Figure 7:
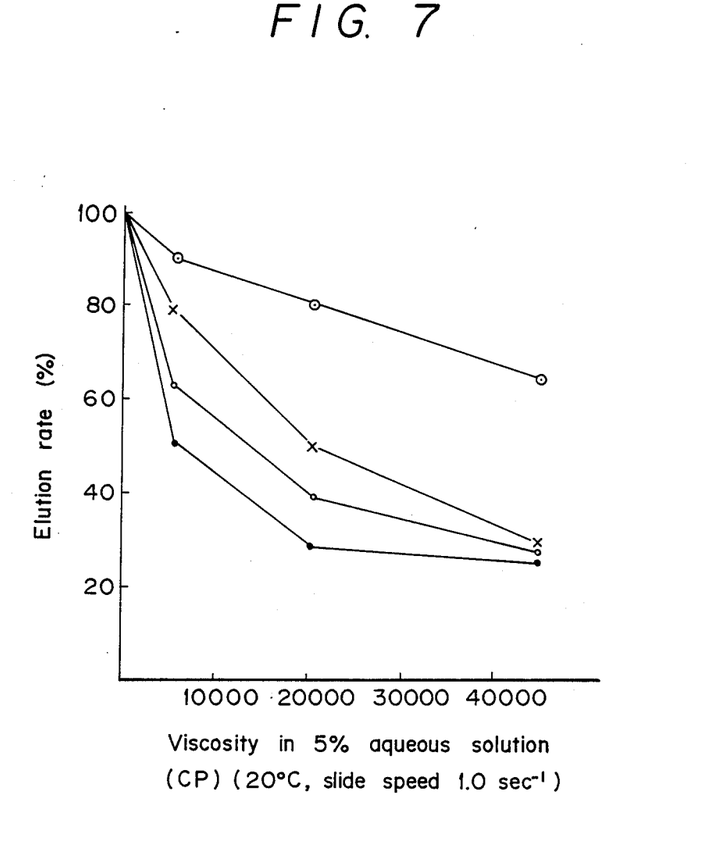

The results are shown in FIG. 7, wherein the full circle ( • ), hollow circle (○), mark (X) and dotted circle (⊙), respectively, represent elution rates after 1, 2, 3 and 18 days. The ChS-C film became instantly dissolved.

It is apparent from FIG. 7 that solubility is reduced as viscosity or crosslinking index is increased.

(3) Retention of film by subcutaneously embedded test in guinea pigs

Each 7.6 mg of the crosslinked ChS-I film and ChS-C film as in the above (1) was embedded into 10 male Hartley strain guinea pigs with 4 weeks of age (an average body weight: 250 g) under the skin of back, incision part was sutured with nylon threads of 5-6 needles and then disinfected. After the 2nd, 5th, 10th and 20th days from transplantation, guinea pigs were killed with ether and then tissue with 3×4 cm was taken out from the under part of the subcutaneous layer of transplanted sites. The tissue thus taken was dipped and extracted into 40 ml of a 4M aqueous solution of guanidine at room temperature for 24 hours under stirring. As control, the tissue of the same part in non-treated guinea pigs was similarly treated.

By a carbazole-sulfuric acid method, uronic acid was measured to determine residual rate. The results are shown in FIG. 8, wherein the hollow circle () and full circle (•) represent, respectively, residual rates of crosslinked ChS-I film and ChS-C film.

Figure 8:
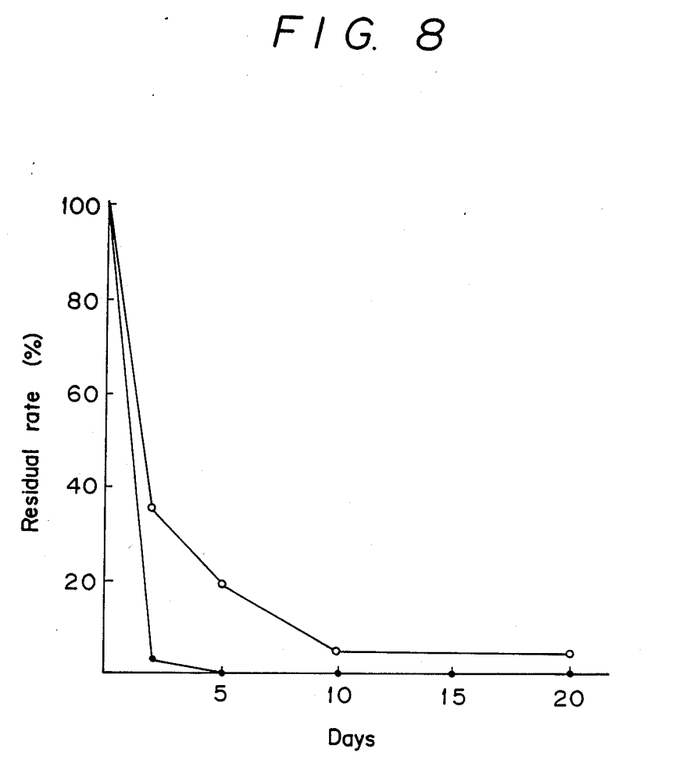

It is apparent from FIG. 8 that the present crosslinked ChS-I film can remain within tissues for a more prolonged period, as compared with the ChS-C film.

Also, it can be seen from the results of the above (2) and (3) that a storage period of crosslinked ChS-C in a living body may be optionally controlled by controlling crosslinking index in crosslinked ChS-C.

EXAMPLE 12

Crosslinked GAG-CO complex film (1) An s-complex of the crosslinked ChS-C as prepared in Example 9 and CO (hereinafter referred to as crosslinked ChS-CO complex) was dissolved in water at a concentration of 1.5% and the resulting solution was coated over a polyvinyl chloride plate to a certain thickness by means of an applicator and dehydrated by heating with a hot air at 40° C. for 20 hours. The coated film was peeled off to obtain a film with a thickness of 0.003 cm.

(2) Male Wistar-strain rats, each group consisting of 4 animals, were used and hair-cut. Then, skin on the back of animal was incised to about 2 cm and immediately sewn by means of Michel sewing apparatus. After sewing, a 2×2 cm square of the film as obtained in the above (1) was placed onto the incised portion, covered with a gauze patch wetted with physiological saline and fixed with a medical tape. After 2 weeks, rats were sacrificed, sewing needles were removed and then a skin strip was prepared with a length of 1 cm. Tensile strength of the skin strip was measured by means of Universal tensile testing instruments TENSILON RTM-50 (available from Toyo-Baldwin K.K.). The film showed tensile resistance of 0.426 kg/cm, which taught a prominent wound healing effect of the crosslinked GAG-CO complex film.

EXAMPLE 13

Test for acute toxicity of s-crosslinked ChS-C

Male ddy strain mice of 4 weeks of age were preliminarily fed over 1 week. At the beginning of test, a body weight of mice used for the test was 20–25 g.

The mice were divided into groups, each group consisting of 15 animals. To each group was intraperitoneally administered the s-crosslinked ChS-C prepared in Example 1 (1) in the form of a 1.5% physiological saline solution thereof at 2 ml/10 g of body weight (crosslinked ChS-C 3000 mg/kg), a 2.5% physiological saline solution thereof at 2 ml/10 g of body weight (crosslinked ChS-C 5000 mg) or a physiological saline solution at 2 ml/10 g of body weight.

Following Irwin method, general manifestations were observed at the same time every day. After 7 days from administration, 5 animals of each group were sacrificed and, after 14 days, remaining survival animals were sacrificed. Administered sites and main organs were visually observed. The results are shown as seen below.

(i) No dead animals were observed in each group.
(ii) There were no difference in the groups administered at 3000 mg/kg and the control groups with regard to general manifestations, changes in body weight, uptake, water intake. The groups administered at 5000 mg/kg showed increase in body weight until 9 days from the administration as compared with the control groups, with maintaining equilibrated state until 14 days.
(iii) There was no difference between the groups administered at 3000 mg/kg and the control groups at autopsy on the 7th day or the 14th day, while there was more uronic acid in intraperitoneal remaining liquid in the groups administered at 5000 mg/kg on both the 7th and 14th days than that in control groups, and it was estimated that the crosslinked ChS-C was left at 1.7–2.0 mg/ml on the 14th day.

(iv) Influence upon organs was hardly observed in every group.

EXAMPLE 14

Test for acute toxicity of s-crosslinked ChS-A

Male ddy strain mice of 4 weeks of age were preliminarily fed over 1 week. At the begining of test, a body weight of mice used for the test was 20–25 g.

The mice were divided into groups, each group consisting of 15 animals. To each group was intraperitoneally administered the s-crosslinked ChS-A prepared in Example 4 in the form of a 1.5% physiological saline solution thereof at 2 ml/10 g of body weight (crosslinked ChS-A 3000 mg/kg), a 2.5% physiological saline solution thereof at 2 ml/10 g of body weight (crosslinked ChS-A 5000 mg) or a physiological saline solution at 2 ml/10 g of body weight.

Following Irwin method, general manifestations were observed at the same time every day. After 7 days from administration, 5 animals of each group were sacrificed and, after 14 days, remaining survival animals were sacrificed. Administered sites and main organs were visually observed. The results are shown as seen below.

(i) No dead animals were observed in each group.

(ii) There were no difference in the groups administered at 3000 mg/kg and the control groups with regard to general manifestations, changes in body weight, uptake, water intake. The groups administered at 5000 mg/kg showed increase in body weight until 9 days from, the administration as compared with the control groups, with maintaining equilibrated state until 14 days.

(iii) There was no difference between the groups administered at 3000 mg/kg and the control groups at autopsy on the 7th day or the 14th day, while there was more uronic acid in intraperitoneal remaining liquid in the groups administered at 5000 mg/kg on both the 7th and 14th days than that in control groups, and it was estimated that the crosslinked ChS-A was left at 1.5–2.2 mg/ml on the 14th day.

(iv) Influence upon organs was hardly observed in every group.

I claim:

1. A crosslinked glycosaminoglycan or a salt thereof obtainable by crosslinking a glycosaminoglycan (provided that hyaluronic acid is excluded) or a salt thereof with a polyfunctional epoxy compound wherein a crosslinking index is 0.005 or more per 1 mole of repeating disaccharides in said glycosaminoglucan and wherein said glycosaminoglycan is chondroitin sulfate, heparin, heparan sulfate, keratan sulfate or keratanpolysulfate and said polyfunctional epoxy compound is epichlorohydrin or epibromohydrin.

2. The crosslinked glycosaminoglycan or a salt thereof as claimed in claim 1 wherein it has a crosslinking index of 0.165 or more per 1 mole of repeating disaccharides in said glycosaminoglycan and is water-insoluble.

3. A pharmaceutical composition for applying to vitreous body comprising an active ingredient in combination with an ophthamologically acceptable carrier or diluent, wherein said active ingredient is a crosslinked glycosaminoglycan or a salt thereof as claimed in claim 1 and is present in such an amount that the viscosity of the composition is not more than 50,000 cp.

4. The composition of claim 3 wherein the viscosity is at least 5,000 cp.

5. The composition of claim 3 wherein the viscosity is 5,000 to 30,000 cp.

6. A pharmaceutical composition for applying to a wound for healing, comprising a wound healing effective amount of the crosslinked glycosaminoglycan or salt thereof, of claim 1, in a pharmaceutically acceptable carrier.

7. The pharmaceutical composition of claim 6 comprising a 2% solution of the crosslinked glycosaminoglycan or salt thereof in a physiological saline solution.

* * * * *